US00PP20981P2

(12) United States Plant Patent
Dümmen

(10) Patent No.: US PP20,981 P2
(45) Date of Patent: May 4, 2010

(54) ***VERBENA* PLANT NAMED 'DUEMPLAVCHA'**
(50) Latin Name: *Verbena hybrida*
Varietal Denomination: Duemplavcha

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 0 days.

(21) Appl. No.: 12/319,345

(22) Filed: Jan. 6, 2009

(51) Int. Cl.
*A01H 5/00* (2006.01)

(52) U.S. Cl. ..... Plt./308
(58) Field of Classification Search ..... Plt./308
See application file for complete search history.

*Primary Examiner*—June Hwu
*Assistant Examiner*—Louanne C Krawczewicz Myers
(74) *Attorney, Agent, or Firm*—C. A. Whealy

(57) ABSTRACT

A new and distinct cultivar of *Verbena* plant named 'Duemplavcha', characterized by its mounding and cascading plant habit; freely branching habit; freely flowering habit; and large lavender and white bi-colored flowers that are held above and beyond the foliage in mounded umbels.

1 Drawing Sheet

Botanical designation: *Verbena hybrida.*
Cultivar denomination: Duemplavcha.

BACKGROUND OF THE INVENTION

The present invention relates to a new and distinct cultivar of *Verbena* plant, botanically known as *Verbena hybrida*, and hereinafter referred to by the name 'Duemplavcha'.

The new *Verbena* plant is a product of a planned breeding program conducted by the Inventor in Rheinberg, Germany. The objective of the breeding program is to create new uniform *Verbena* plants with large and attractive flowers.

The new *Verbena* plant originated from a self-pollination made by the Inventor in August, 2005 in Rheinberg, Germany of a proprietary selection of *Verbena hybrida* identified as code number V04-1309-3, not patented. The new *Verbena* plant was discovered and selected by the Inventor as a single flowering plant within the progeny of the stated self-pollination in a controlled greenhouse environment in Rheinberg, Germany in May, 2007.

Asexual reproduction of the new *Verbena* plant by terminal cuttings in a controlled greenhouse environment in Rheinberg, Germany since May, 2007 has shown that the unique features of this new *Verbena* plant are stable and reproduced true to type in successive generations.

SUMMARY OF THE INVENTION

Plants of the new *Verbena* have not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Duemplavcha'. These characteristics in combination distinguish 'Duemplavcha' as a new and distinct cultivar of *Verbena:*

1. Mounding and cascading plant habit.
2. Freely branching habit.
3. Freely flowering habit.
4. Large lavender and white bi-colored flowers that are held above and beyond the foliage in mounded umbels.

Plants of the new *Verbena* differ from plants of the parent selection in the following characteristics:

1. Plants of the new *Verbena* are more freely branching than plants of the parent selection.
2. Plants of the new *Verbena* and the parent selection differ in flower color.

Plants of the new *Verbena* can be compared to plants of the *Verbena hybrida* 'Swestrena', disclosed in U.S. Plant Pat. No. 17,712. In side-by-side comparisons conducted in Rheinberg, Germany, plants of the new *Verbena* differed from plants of 'Swestrena' in the following characteristics:

1. Plants of the new *Verbena* had larger leaves than plants of 'Swestrena'.
2. Plants of the new *Verbena* had larger flowers and larger umbels than plants of 'Swestrena'.
3. Plants of the new *Verbena* and 'Swestrena' differed slightly in flower color.

BRIEF DESCRIPTION OF THE PHOTOGRAPH

The accompanying colored photograph illustrates the overall appearance of the new *Verbena* plant, showing the colors as true as it is reasonably possible to obtain in colored reproductions of this type. Colors in the photograph may differ slightly from the color values cited in the detailed botanical description which accurately describe the colors of the new *Verbena*.

The photograph comprises a close-up view of typical leaves and flowers of 'Duemplavcha'.

DETAILED BOTANICAL DESCRIPTION

The aforementioned photograph and following observations, measurements and values describe plants grown in 13-cm containers in Rheinberg, Germany in a glass-covered greenhouse during the summer and under conditions which closely approximate commercial production. During the production of the plants, day and night temperatures averaged 18° C. and light levels averaged 4,500 lux. Plants were pinched one time about one week after planting. Plants had been growing for four months when the photograph and the description were taken. In the description, color references are made to The Royal Horticultural Society Colour Chart, 1995 Edition, except where general terms of ordinary dictionary significance are used.

Botanical classification: *Verbena hybrida* 'Duemplavcha'.

Parentage:

*Female, or seed, parent.*—Proprietary selection of *Verbena hybrida* identified as code number V04-1309-3, not patented.

*Male, or pollen, parent.*—Proprietary selection of *Verbena hybrida* identified as code number V04-1309-3, not patented.

Propagation:

*Type.*—Terminal cuttings.

*Time to initiate roots, summer and winter.*—About ten days at 20° C.

*Time to produce a rooted young plant, summer.*—About 21 days at 20° C.

*Time to produce a rooted young plant, winter.*—About 25 days at 20° C.

*Root description.*—Fine, fibrous; white in color.

*Rooting habit.*—Freely branching; dense.

Plant description:

*Plant habit.*—Initially upright, then mounding to cascading plant habit. Freely branching habit with about four to six primary lateral branches with secondary lateral branches potentially forming at every node; pinching enhances lateral branch development; dense and bushy plant habit. Moderately vigorous growth habit.

*Plant height.*—About 15 cm.

*Plant diameter.*—About 20 cm.

Lateral branch description:

*Length.*—About 16 cm.

*Diameter.*—About 2 mm.

*Internode length.*—About 4 cm.

*Texture.*—Pubescent.

*Color.*—Close to 144A.

Foliage description:

*Arrangement.*—Opposite, simple.

*Length.*—About 4.3 cm.

*Width.*—About 2.5 cm.

*Shape.*—Lanceolate.

*Apex.*—Acute.

*Base.*—Attenuate.

*Margin.*—Lobed.

*Texture, upper and lower surfaces.*—Pubescent, coarse.

*Venation pattern.*—Pinnate.

*Color.*—Developing and fully expanded leaves, upper surface: Close to 146A; venation, close to 146D. Developing and fully expanded leaves, lower surface: Close to 146B; venation, close to 146D.

*Petiole length.*—About 4.2 mm.

*Petiole diameter.*—About 1.6 mm.

*Petiole texture, upper and lower surfaces.*—Smooth.

*Petiole color, upper surface.*—Close to 146A.

*Petiole color, lower surface.*—Close to 146B.

Flower description:

*Flower arrangement and habit.*—Salverform flowers arranged in hemispherical terminal umbels; umbels dense and mounding; numerous umbels covering the entire plant. Flowers face upward or outward. Freely flowering habit with about 20 flowers and flower buds per inflorescence. Flowers not fragrant.

*Natural flowering season.*—Plants flower continuously from the spring through the fall in Germany. Plants begin flowering about eight weeks after planting.

*Flower longevity.*—Individual flowers last about one week on the plant; flowers persistent.

*Inflorescence size.*—Height: About 3 cm. Diameter: About 6 cm.

*Flowers.*—Appearance: Flared trumpet, corolla fused, five-parted. Diameter: About 2.6 cm. Depth: About 2.6 cm.

*Flower buds.*—Length: About 1.5 cm. Diameter: About 3.5 mm. Shape: Oval, tubular. Color: Close to 146A.

*Corolla.*—Arrangement: Single whorl of five fused petals. Petal lobe length: About 3.1 cm. Petal lobe width: About 8 mm. Petal lobe shape: Obovate. Petal lobe apex: Emarginate to cordate. Petal margin: Entire. Petal texture, upper and lower surfaces: Smooth, glabrous; velvety. Color: When opening and fully opened, upper surface: Close to 66D; towards the base, close to 155B; color does not fade with development. When opening and fully opened, lower surface: Close to 75A.

*Calyx.*—Arrangement: Star-shaped calyx with five fused sepals. Sepal length: About 1.4 cm. Sepal width: About 1 mm. Sepal shape: Ligulate. Sepal apex: Acute. Sepal margin: Entire. Sepal texture, upper and lower surfaces: Pubescent, coarse. Sepal color, upper and lower surfaces: Between 146D and 144A.

*Peduncles.*—Length: About 7.3 cm. Diameter: About 2 mm. Strength: Strong. Texture: Pubescent. Color: Close to 144A.

*Pedicels.*—Length: About 0.5 mm. Diameter: About 0.5 mm. Strength: Strong. Texture: Smooth, glabrous. Color: Close to 144A.

*Reproductive organs.*—Stamens: Quantity/arrangement: About four to five per flower, adnate to corolla tube. Anther shape: Oval. Anther length: About 0.75 mm. Anther color: Close to 144B. Pollen amount: Moderate. Pollen color: Close to 2D. Pistils: Quantity: One per flower. Pistil length: About 1.7 cm. Stigma shape: Bi-parted. Stigma color: Close to 144A. Style length: About 1.6 cm. Style color: Close to 144D. Ovary color: Close to 144C. Fruits/seeds: Fruit and seed development has not been observed.

Temperature tolerance: Plants of the new *Verbena* have been observed to tolerate temperatures from about 5° C. to about 35° C.

Pathogen/pest resistance: Plants of the new *Verbena* have not been observed to be resistant to pathogens and pests common to *Verbenas*.

It is claimed:

1. A new and distinct *Verbena* plant named 'Duemplavcha' as illustrated and described.

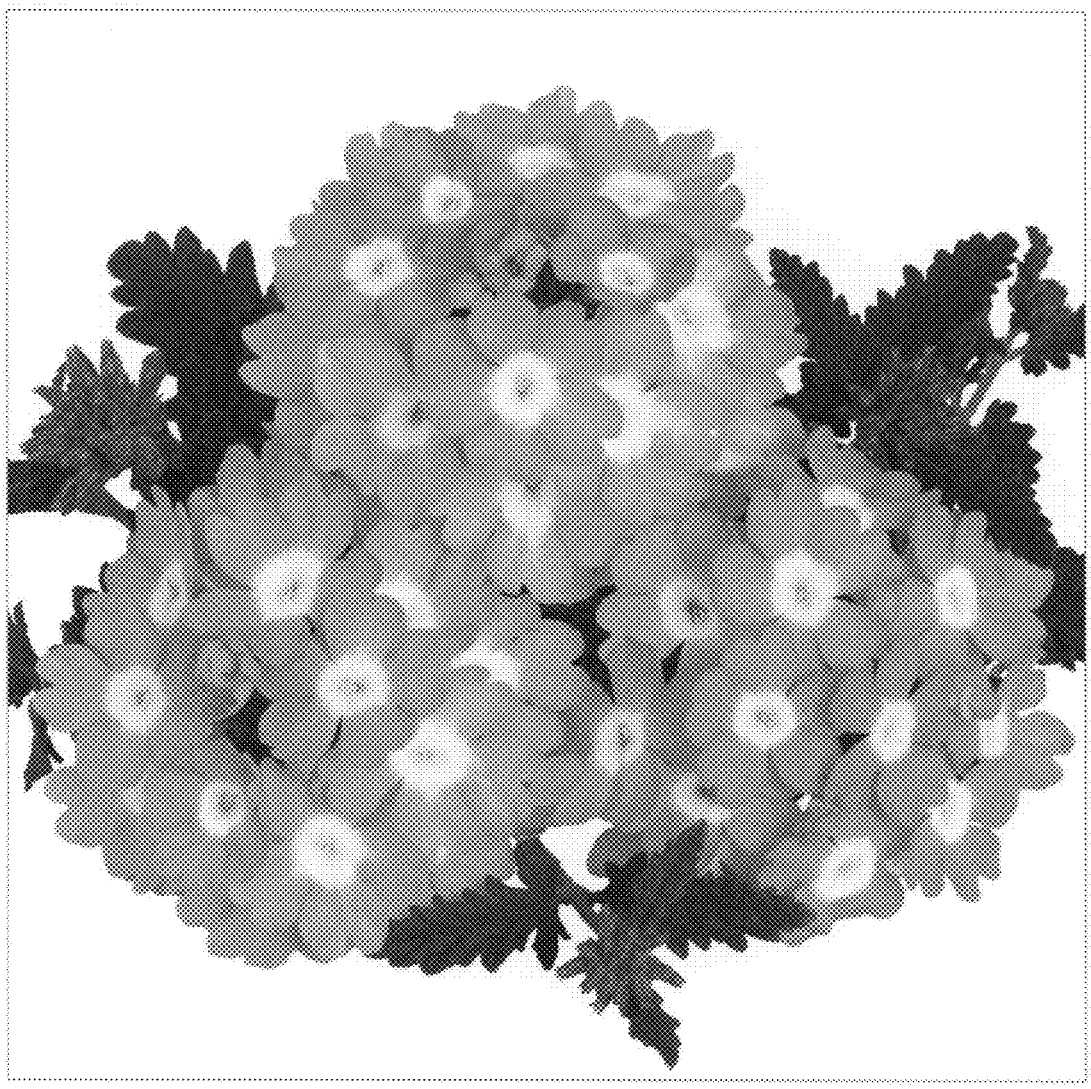

* * * * *